United States Patent [19]

Hara et al.

[11] Patent Number: 5,912,152
[45] Date of Patent: Jun. 15, 1999

[54] PROCESS FOR PREPARING SPHINGOMYELIN AND CERAMIDE FROM ERYTHROCYTE AS A STARTING MATERIAL AND A CURING AGENT OR COSMETIC FORMULATED WITH CERAMIDE

[75] Inventors: Susumu Hara, Hino; Hidehiko Takahashi, Tokyo; Yumiko Tomiya, Tanashi, all of Japan

[73] Assignee: Yakurigaku Chuo Kenkyusho, Tokyo, Japan

[21] Appl. No.: 08/607,316

[22] Filed: Feb. 26, 1996

[30] Foreign Application Priority Data

Feb. 28, 1995 [JP] Japan .................................. 7-039840
May 31, 1995 [JP] Japan .................................. 7-134332

[51] Int. Cl.$^6$ ............................. C12P 13/00; C12P 1/00
[52] U.S. Cl. ..................................... 435/128; 435/834
[58] Field of Search ............................. 424/93.73, 520, 424/529, 533; 435/128, 834

[56] References Cited

U.S. PATENT DOCUMENTS

| | | | |
|---|---|---|---|
| 4,525,458 | 6/1985 | Imamura et al. | 435/196 |
| 5,206,020 | 4/1993 | Critchley et al. | 424/401 |
| 5,206,355 | 4/1993 | Richards et al. | 536/4.1 |
| 5,326,565 | 7/1994 | Critchley et al. | 424/401 |
| 5,415,855 | 5/1995 | Critchley et al. | 424/61 |
| 5,466,782 | 11/1995 | Rousset | 530/374 |
| 5,476,671 | 12/1995 | Cho et al. | 424/70.1 |
| 5,525,709 | 6/1996 | Davey et al. | 554/68 |
| 5,532,141 | 7/1996 | Holler | 435/74 |
| 5,683,684 | 11/1997 | Montastier et al. | 424/78.03 |

FOREIGN PATENT DOCUMENTS

| | | |
|---|---|---|
| 2 700 953 | 8/1994 | France . |
| 64-16708 | 1/1989 | Japan . |
| 6-7161 | 1/1994 | Japan . |
| 8-217658 | 8/1996 | Japan . |
| WO 92/17160 | 10/1992 | WIPO . |

OTHER PUBLICATIONS

Hakomori et al. Isolation and Characterization of Glycosphingolipid From Animal Cells and Their Membranes. Methods in Enzymology, 32(Biomembranes, Part B), pp. 345–367. (1974).

Sako et al. Characterization of Neutral Glycosphingolipids From Porcine Erythrocyte Membranes. International Journal of Biochemistry. vol. 19, No. 10, pp. 923–929. (1987).

Miller–Podraza et al. New Method for the Isolation of Polyglycosylceramides From Human Erythrocyte Membranes. Biochimica et Biophysica Acta, 1168(3) pp. 330–339. (1993). Full Document.

Makoto Ito et al. Specific Hydrolysis of Intact Erythrocyte Cell–Surface Glycosphingolipids By Endoglycoceramidase. Eur. J. Biochem. 218, pp. 637–643. (1993) Full Document.

Y. Z. Frohwein and S. Gatt: "Enzymatic Hydrolysis of Sphingolipids" Biochemistry, vol. 6, No. 9, 1967, pp. 2783–2787, XP000654511.

(List continued on next page.)

*Primary Examiner*—Robert H. Harrison
*Attorney, Agent, or Firm*—Armstrong, Westerman, Hattori, McLeland & Naughton

[57] ABSTRACT

A process for the preparation of ceramide by using erythrocytes as a starting material is disclosed herein. For the purpose of obtaining ceramide at a low cost and in a large amount, ceramide is prepared by means of hydrolysis or enzymolysis of sphingolipid existing in sphingomyelin. According to the preparation process of the present invention, ceramide useful as a moisturizer for human skin can be obtained at a low cost and in a large amount by relying upon erythrocytes as a starting material.

4 Claims, 4 Drawing Sheets

OTHER PUBLICATIONS

J. J. Myher et al.: "Molecular Species of Glycerophospholipids and Sphingomyelins of Human Erythrocytes: Improved Method of Analysis." LIPIDS, vol. 24, No. 5, 1989, pp. 396–407, XP000654439.

P. V. Reddy et al.: "Hydrolysis of Sphingomyelin to Ceramide with Hydrofluoric Acid." Chem. Phys. Lipids, vol. 17, 1976, pp. 373–377, XP000654512.

Chemical abstracts, vol. 119; 1993, abstract 134957b.

Chemical abstracts, vol. 119, 1993, abstract 265889d.

Supplement to the Japanese Cosmetic Ingredients Codex 1993, "523019 Bovine Brain Abstract", p. 80 and "523917 Bovine Brain Lipid", pp. 78–79.

P.V. Reddy, Chem. Phys. Lipids., 17, (1976) pp. 373–377.

PROCESS FOR PREPARING SPHINGOMYELIN AND CERAMIDE FROM ERYTHROCYTE AS A STARTING MATERIAL AND A CURING AGENT OR COSMETIC FORMULATED WITH CERAMIDE

BACKGROUND OF THE INVENTION

1. Field of the Invention

The present invention relates to a process for the preparation of ceramide utilized as a skin moisture-keeping component, and provides a process for acquiring ceramide cheaply and in bulk, which has been hithertofore unknown.

2. Prior Art

It is known that nerve tissue of mammal contains sphingolipid which is a ceramide derivative. The sphingolipid of bovine brain is utilized as it is, without conversion to ceramide, as a crude material for cosmetics. (cf. Official Gazette of Patent Kokai Shō 64-16708. Supplement to the Japanese Cosmetic Ingredients Codex 1993 "523019 Bovine Brain Extract" and "523017 Bovine Brain Lipid").

On the other hand, the following references report a process for decomposing sphingolipid to obtain ceramide:

Hydrolysis by using hydrogen fluoride (cf. Reddy, P. V.; Natarajan, V; Sastry, P. S.: Chem. Phys. Lipids, 1976, 17, 373–7).

Enzyme-decomposition by means of phospholipase produced by bacteria.

However, there has not been reported any process for preparation of ceramide by applying these methods.

No process has ever been established, in which ceramide is cheaply acquired from sphingolipid by using erythrocytes of cattle and poultry as starting materials.

Human rough skin occurs when moisture has been lost due to dermatitis and the like or under a physiological requirement and dry environments, etc. Rough skin is of course not only an aesthetic problem but also dermatologically undesirable because of a decrease in the protective action which the skin has.

For curing such a rough skin, medicines for external use such as ointments, lotions, etc. and cosmetics such as creams, milky lotions, etc. may be used. These pharmaceutical preparations or cosmetic formulations functionally keep skin in a healthy state at around 20% moisture thereof. For this purpose are used emulsifiable base agents having a function resembling a sebum cutaneum membrane existing on the skin, and lactic acid existing in the skin, and components of so-called natural moisturing factors (NMF) such as pyrrolidone carboxylate, amino acids, etc.

Recently, it has been found that the stratum corneum intercellular lipid, which is mainly composed of ceramide, promotes retention of skin moisture. Addition of a sufficient amount of ceramide can strengthen the effect of a preparation for rough skin. Accordingly, it has been desired to cheaply supply large quantities of ceramide.

Sphingolipids (ceramide derivatives such as sphingomyelin, glucosylceramide, etc.) used as a raw material have until now been said not to exist in the stratum corneum intercellular lipid. Such substances contain large highly polar substituents such as phosphorylcholine, saccharide, etc. which are much different in property from ceramide. In order to supplement the inherent water-retention function which the skin has, the present inventors have aimed at the application of ceramide per se and devoted themselves to studying the processes of preparing ceramide. As a result, they have developed a process wherein sphingolipid is efficiently extracted from living materials, which is further followed by conversion to ceramide.

For such purpose, various sources of readily available raw material for obtaining ceramide have firstly been pursued.

Heretofore, raw materials for sphingolipid were sought from nerve tissues such as bovine brain and the like, as mentioned above in Japanese Patent Kokai Shō 64-16708 and its cited literatures, and also in the Supplement to the Japanese Cosmetic Ingredients Codex 1993 "Bovine Brain Extract", "Bovine Brain Lipid", etc. However, such a source is expensive because of the limited amounts available, and therefore, sufficient necessary amounts are supplied only with difficultly. From such a viewpoint, the present inventors have paid attention to erythrocyte as source of ceramide.

Cattle and poultry are bred on a large scale for food. Accordingly it is well known fact that a large amount of blood is released every time they are butchered. For use in tissue culture and the like, blood serum and plasma protein are produced from blood in large quantities. In addition, from hemocytes which were left after obtaining blood serum, hemoglobin is extracted to be utilized as medicines and foods. On the other hand, the finally remaining erythrocyte membrane after the production of blood serum and hemoglobin from blood is now of no use and therefore, such a membrane will be discarded with much expense at the present stage.

SUMMARY OF THE INVENTION

As a result of extensive research on methods for effective extraction of sphingolipid from such an erythrocyte membrane, the inventors have succeeded in obtaining a highly pure sphingomyelin in good yield with a smaller number of steps and use of a cheap solvent, by means of decomposing and removing glycerophospholipid from highly polar lipids. In addition, the present inventors have also developed a novel technique wherein erythrocyte membrane is first inoculated with bacteria to convert sphingomyelin in the membrane directly to ceramide, which is followed by extraction thereof.

DETAILED DESCRIPTION OF THE INVENTION

The erythrocyte membrane, from which the lipids were extracted according to the system of the present invention, is lowered to about ¾ weight (dry weight) and further compressed to an odorless solid having little water content. Accordingly, such residue will be readily converted to a high protein feed or fertilizer. After all, it will bring an additional value to the removed materials and also prevent pollution of the environment to utilize erythrocyte as a raw material of ceramide.

The methods for obtaining ceramide from sphingomyelin were then investigated. It is known that sphingomyelin can be converted specifically to ceramide by means of phospholipase C or sphingomyelinase, and that Phospholipase is produced by bacteria such as *Clostridium perflingens, Bacillus cereus,* etc.

Since a bond between the primary hydroxyl group of ceramide with choline phosphate ester is relatively stable against a chemical hydrolysis, it was decided to break the bond, using an enzyme.

The above-mentioned phospholipase prepared from bacteria is available commercially as a reagent grade but it is too expensive to use in an industrial application (cf. 1000 unit (about 10 mg) costs around $200). On the contrary, the phospholipase in the present invention is utilized, while being reproduced at a low cost in a simple method, because B. cereus is cultivated in the raw material per se of ceramide or in bouillon which is the most popular and fundamental liquid culture medium. Further, utilization of a bio-reactor holding activities of these enzymes has made efficient operation of the ceramide production possible.

Cholesterol exists in erythrocyte in an amount comparable to that of sphingomyelin. Since the polarity of cholesterol is very similar to that of ceramide, the crude ceramide prepared by the present process will become a mixture of ceramide and cholesterol.

On the other hand, the stratum corneum intercellular lipid, which has the function of holding moisture in the skin, contains ceramide and cholesterol as main components. It is known to firmly hold bound water due to the coexistence of such components.

Accordingly, the fact of a mixture of cholesterol and ceramide is rather suitable as a moisturizing agent for the skin.

However, when erythrocyles of pig and the like are sought as the source, a certain degree of amounts of cholesterol should be removed at the stage prior to the production of ceramide from sphingomyelin, because the cholesterol ratio will be somewhat higher. For that reason, a solvent extraction has been investigated. As a result when the precipitate resulting from the residue of heme-iron was washed with various kinds of organic solvent such as diethyl ether, dichloromethane, hexane, benzene and cyclohexane, it was found that upon the dichloromethane washing, the cholesterol extraction factor was peculiarly high along with a lower loss of sphingomyelin.

DESCRIPTION OF THE PREFERRED EMBODIMENTS

Figure 1A:
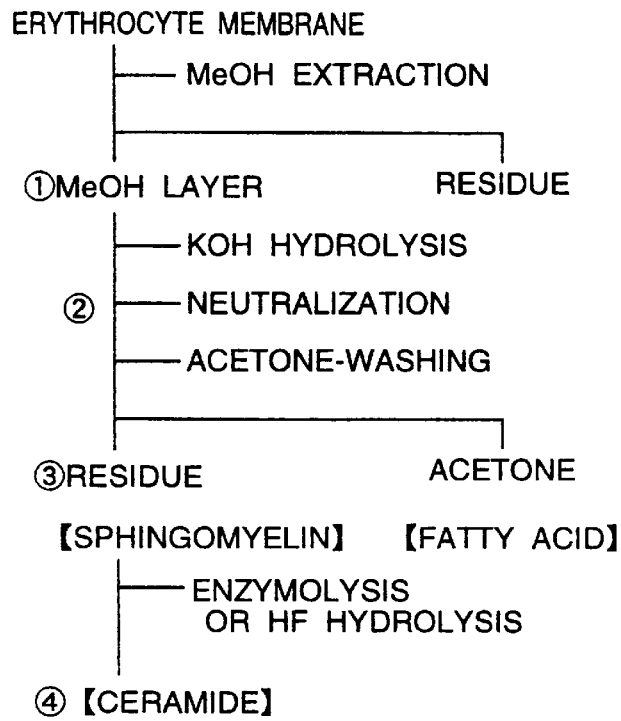
FIG. 1A is a flow chart showing the working examples of the present invention.
Figure 1B:
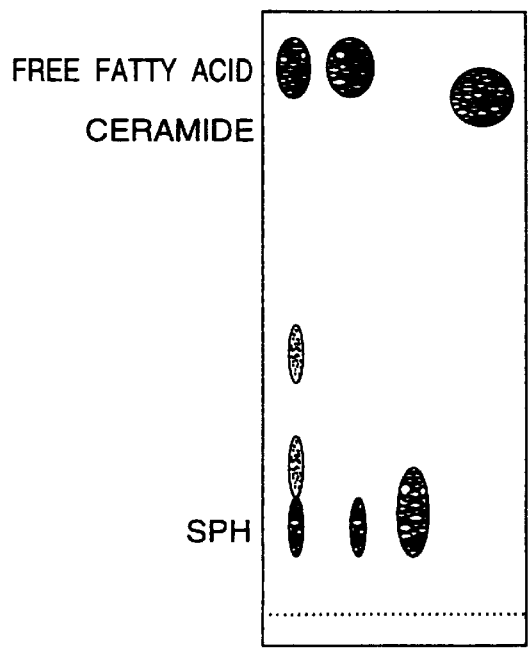
FIG. 1B is a TLC development on the product of the present invention. Developing solvent is $CHCl_3:Me_2CO:MeOH:AcOH:H_2O=10:4:2:2:1$. In the figure, Sph means sphingomyelin.
Figure 2:
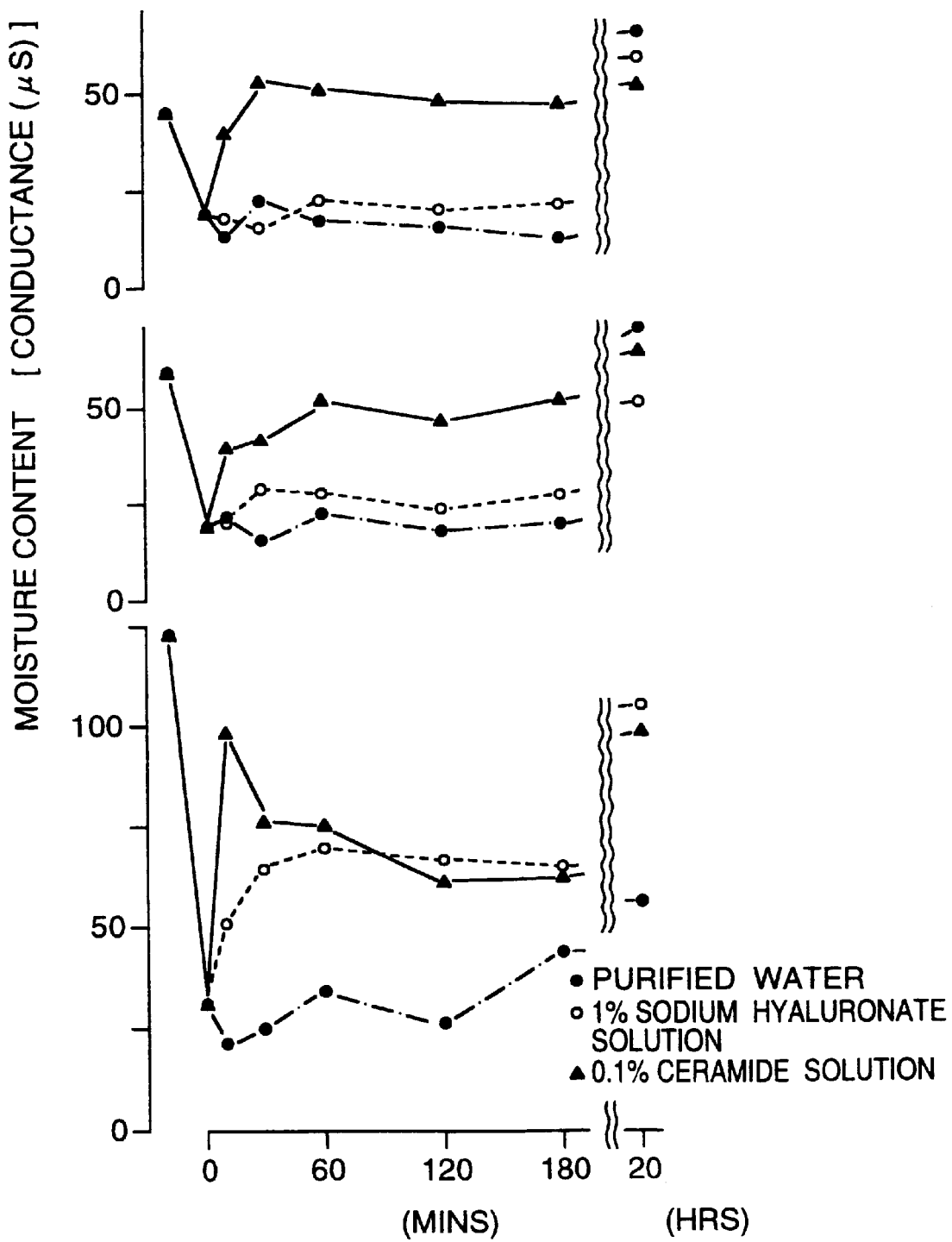
FIG. 2 shows, as graphs, the improvement effect of ceramide, with respect to the moisture-keeping function of a rough skin experimentally formed.
Figure 3:
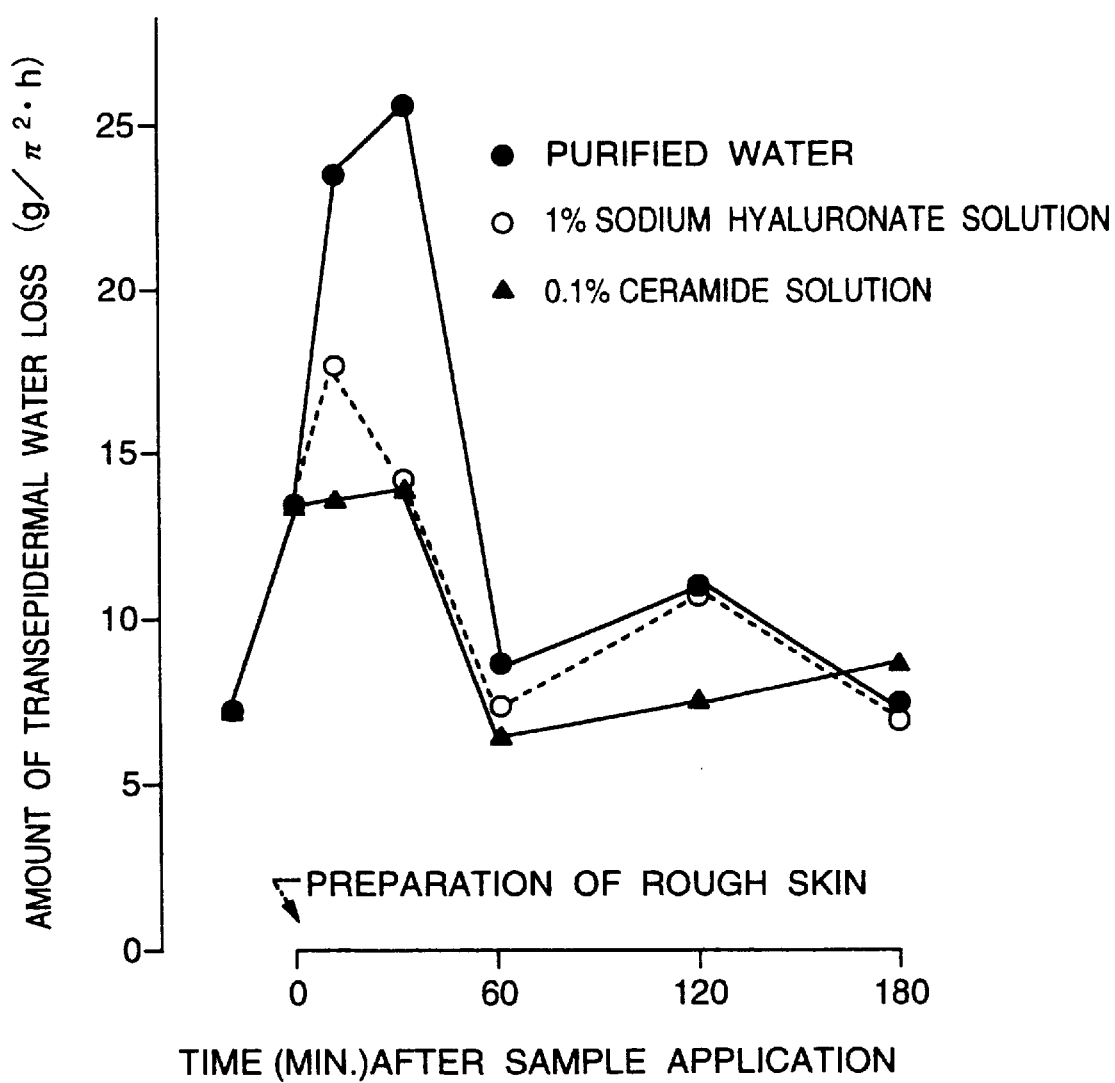
FIG. 3 shows, as a graph, the improvement effect of ceramide, with respect to a barrier function of a rough skin experimentally formed.
Figure 4:
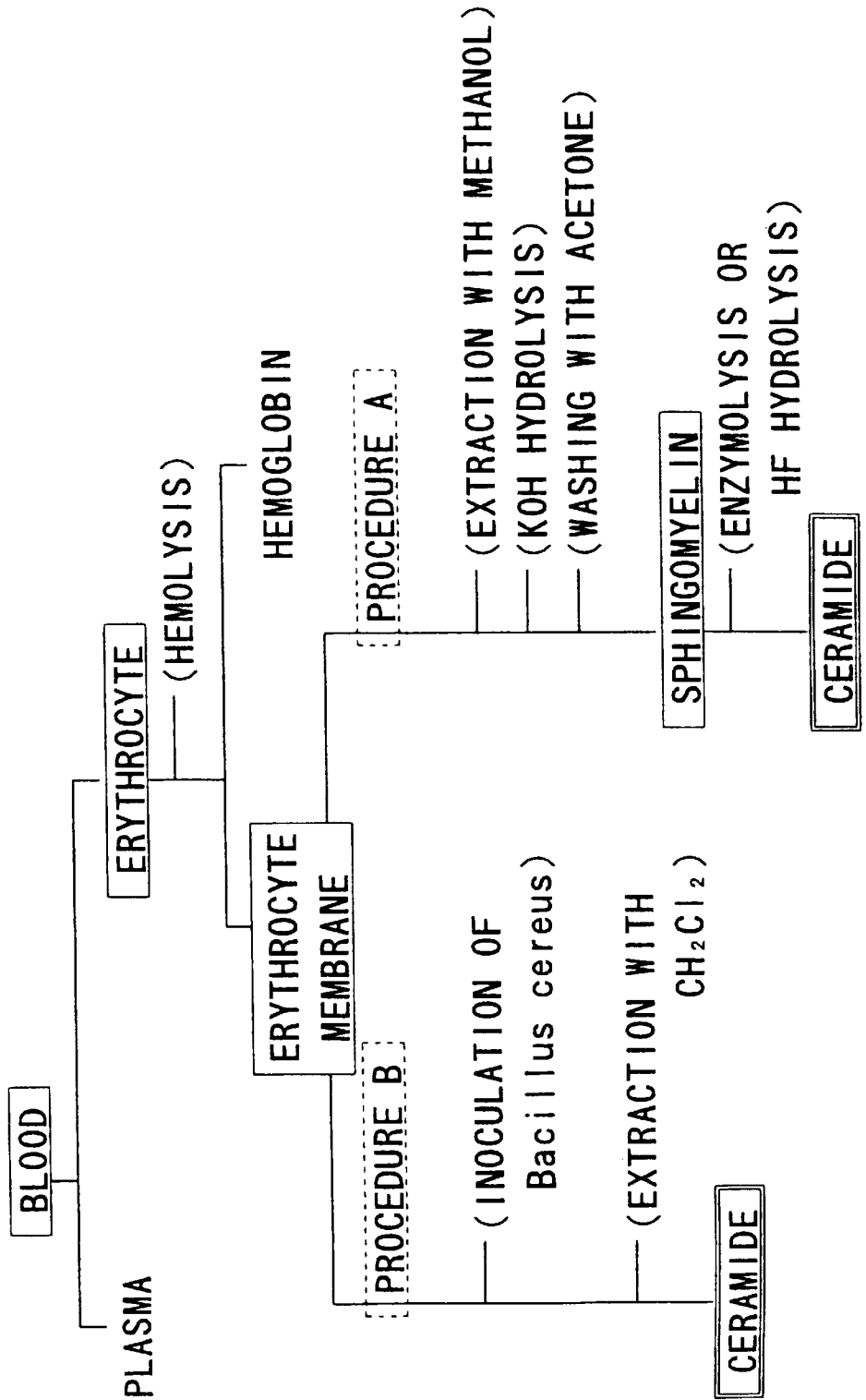
FIG. 4 is the production flow chart including the original and the second inventions (corresponding to the two priority applications, JP-7-039840 and JP-7-134332). A indicates the steps for the former and B indicates the steps for the latter.

The present invention will be explained relying upon its preferred embodiments as follows:

EXAMPLE 1

This example shows a process for the preparation of ceramide from the residue occurring upon the preparation of heme-iron from erythrocytes.

The liquid remaining upon separation of hemoglobin from pig erythrocyte was neutralized by adding a necessary amount of disodium hydrogenphosphate. Then, from the produced precipitate 10 ml thereof was taken up, which was followed by inoculation thereon of Bacillus cereus (IAM 1208), and thereafter by cultivation, while shaking for 20 hours. Then, 5 ml of dichloromethane was added to the precipitate and stirred for 2 hours at 30° C. The dichloromethane layer was separated out and then the precipitate was further extracted with dichloromethane. The organic layer in a lump was subjected to a vacuum distillation, whereby 81 mg of crude ceramide was obtained.

The additives for neutralization are not limited to disodium hydrogenphosphate, but regardless of type, as long as acids, bases and their salts have a buffer function.

EXAMPLE 2

This example shows a process for extracting lipid from erythrocyte membrane and further isolating sphingomyelin.

A collected bovine blood, to which EDTA $Na_2$ was added, was subjected to a centrifuge to obtain erythrocytes. To the obtained erythrocytes was added 0.2% acetic acid in ten times amount, thereby causing hemolysis, which was then subjected to a centrifuge to obtain precipitates. The precipitates were further sufficiently water-washed to obtain erythrocyte membrane.

4.00 g of freeze-dried bovine erythrocyte membrane was put in Soxhlet extraction vessel, and then extracted two times with 200 ml of methanol. The extract liquid was cooled to room temperature, and then potassium hydroxide was added thereto for dissolution so as to make up the solution of 0.1M concentration, which was then left for two hours at room temperature. The excess alkali was neutralized with a concentrated hydrochloric acid, and thereafter, the solvent was distilled off under a reduced pressure. The resulting solid lipid was well washed with acetone to obtain 0.69 g of sphingomyelin.

With respect to erythrocyte membranes of sheep and pig, sphingomyelin was also obtained in a similar manner to the above.

EXAMPLE 3

This example shows a method of preparing ceramide from sphingomyelin in a batch operation using a culture medium of bacteria.

Bacillus cereus (IAM 1208) was inoculated in a conventional bouillon and shake-culture was conducted for 20 hours. The culture medium was subjected to a centrifuge (18000 rpm. 30 minutes) and then its supernatant liquid was withdrawn therefrom. After 100 mg of sphingomyelin was added to the supernatant liquid and sufficiently dispersed, further 5 ml of diethylether was added thereto, and then the mixture was reacted for 18 hours while being stirred at 30° C. After completion of the reaction, the ether layer was separated and taken up. The reaction solution was further extracted with ether, and then the total organic layer was distilled off under a reduced pressure to obtain 51 mg of crude ceramide.

EXAMPLE 4

This example shows preparation of ceramide from sphingomyelin in a batch operation system using a crude enzyme prepared from a culture medium of Bacillus cereus.

Bacillus cereus was inoculated in a conventional bouillon and shake-cultured at 30° C. for a day. Then, 5000 g of the culture medium was subjected to a centrifuge for 20 minutes, and then a supernatant liquid was salted out with 70% saturated ammonium sulfate solution to separate a precipitate therefrom thereby obtaining a crude enzyme.

To 67 mg of sphingomyelin, 5 ml of 0.1M tris buffer solution (pH 7.4) was added. Further, 10 mg of a crude enzyme resulting from *Bacillus cereus* and 5 ml of diethylether were added thereto, and then the mixture was reacted for 18 hours while being stirred at 37° C. After completion of the reaction, the ether layer was separated and further the reaction solution was extracted with ether. The total of organic layer was distilled off under a reduced pressure to obtain 32 mg of crude ceramide.

EXAMPLE 5

This example shows preparation of ceramide from sphingomyelin in continuous operation system using a column in which an immobilized enzyme was filled.

10 g of Amberlite XAD-8 and 500 mg of crude enzyme obtained from a culture medium of *Bacillus cereus* were incorporated into 50 ml of 0.1M tris-buffer solution (pH 7.4) while being stirred for 5 hours. Adsorbed immobilized-enzyme was filtered and gathered, and then washed with 20 ml of 0.1M tris buffer solution (pH 7.4) containing 0.03M $CaCl_2$.

Through a column having been packed with the immobilized enzyme wetted with the buffer solution, diethylether saturated with 0.1M tris buffer solution (pH 7.4), which contains 0.03M $CaCl_2$ containing 1.7 mg/ml conc. sphingomyelin, was made to flow down at a flow rate of 0.4 ml/min. for 72 hours. The recovered solution was incorporated with a saturated NaCl solution and ether while being vigorously stirred. An organic layer thereof was then separated and further the remaining portion was extracted with ether added thereto. Solvent of the total organic layers was distilled off in vacuo to obtain 2.45 g of crude ceramide.

EXAMPLE 6

The crude ceramide prepared from pig erythrocyte by the method of Example 1 contains cholesterol. In order to control such amounts of cholesterol, 10 ml of the precipitate produced by neutralizing the remaining liquid obtained by separating hemoglobin from pig erythrocytes was washed with the same quantity of dichloromethane. The precipitate was further subjected to treatment by high pressure steam vapor sterilization, which was followed by inoculating *Bacillus cereus* therein. Thereafter, the operation similar to the manner in Example 1 was conducted.

The following table shows the result of analysis of the ratio of cholesterol vs. ceramide in the obtained crude ceramide, depending on the absence and the presence of washing treatment with dichloromethane:

| | Cholesterol | Ceramide (%) |
|---|---|---|
| Untreated | 58.3 | 37.4 |
| Washed with dichloromethane | 29.3 | 65.2 |

EXAMPLE 7

0.1% solution of ceramide dissolved in propylene glycol was applied to the eye-corners of five female patients, and influence on wrinkles (crow's foot) was observed.

Evaluation of the effect was based upon the following observation:

Reliefs made of a dental quick dry resin (commercial name "Exafine") were manufactured before and after the treatment to observe the depth and number of wrinkles under a microscope. The following table is the summarization of results of two-month application with the above ceramide solution:

| Age | Depth (decrease) | Number (decrease) |
|---|---|---|
| 43 | ++ | + |
| 37 | ++ | + |
| 50 | ++ | ± |
| 48 | ++ | ++ |
| 45 | ++ | ++ |

Degrees of decrease on depth and number of wrinkles after the treatment for two months.

EXAMPLE 8

To skins of healthy normal males, which skins were experimentally made in so-called rough skin state by removing intercellular lipid, ceramide was applied. Then, confirmation was made on whether or not the skin physiological function can be supplemented or recovered by means of ceramide.

In order to observe recovery of moisture-keeping function in rough skin, three portions (round shape, 2 cm diameter) on the left forearm of healthy normal males (n=3) were exposed to acetone-ether (1:1) for 10 minutes to remove intercellular lipid. Then, to the three portions were applied purified water, 1% sodium hyaluronate solution and 0.1% ceramide solution, respectively. Corneal layer (stratum corneum) surface high frequency conductivity was time-sequentially determined as an index of moisture content of the corneal layer (SKICON 200, IBS Co., Ltd.). The determination was carried out in a constant temperature room at 20° C. under 60% humidity.

The effect of ceramide on moisture-retention by the human keratin layer is shown in FIG. 1.

The skins, in which the moisture content of stratum corneum was remarkably lowered by removing the intercellular lipid with an organic solvent, soon recovered the moisture-retaining function in every case, owing to application of 0.1% ceramide solution. The latter effect was superior to that in the case of the 1% sodium hyaluronate solution.

EXAMPLE 9

In the state of rough skin similar to that as mentioned in Example 1, the improved effect in barrier function against transepidermal water loss amount (TWL) was evaluated with respect to ceramide.

TWL in the rough skin induced by the manner similar to that in Example 1 was time-sequentially pursued using an Evaporimeter (Servo Med. Co., Ltd.) to survey the effect of ceramide. Determination was conducted in a constant temperature room at 20° C. under 60% humidity.

The improvement in effect of barrier function of ceramide against transepidermal water loss was shown in FIG. 2. The TWL values elevated by the rough skins experimentally formed exhibited an improvement, owing to application of 0.1% ceramide solution, whose effect was slightly stronger than in the case of 1% sodium hyaluronate solution. After 3 hrs from application of ceramide, TWL values returned to those of healthy normal skins.

EXAMPLE 10

A hydrophilic ointment incorporated with 0.1% ceramide was applied to four atopic dermatitis patients two times in the morning and evening each day. Then, the curing effects were observed.

A curing experiment term was set in the winter season, during which keratosis usually becomes worse due to coldness and dryness.

Recovering degree of atopic dermatitis was judged according to the following standard:

Notably effective . . . Perfect healing.

Valid . . . Improvement was exhibited in almost symptoms.

Slightly valid . . . Some improvement was exhibited.

Invalid . . . No change or ingravescence.

Detailed results of symptom examples were tabulated as follows:

| No. | Sex | Age | Location | Curing term | Effect |
|-----|-----|-----|----------|-------------|--------|
| 1 | F | 13 | whole body | 3 weeks | valid (smarting) |
| 2 | M | 9 | legs and arms | 3 months | valid (ibid) |
| 3 | M | 7 | legs and arms | 3 months | valid (ibid) |
| 4 | F | 10 | whole body | 3 months | valid |

(Summary)

Application of the hydrophilic ointment incorporated with 0.1% ceramide to patients of atopic dermatitis exhibited excellent curing effects as much as 100% beyond validation.

We claim:

1. A process for preparing N-lignoceroylsphingosine, comprising:

(1) separating erythrocyte membranes from heme-iron by hemolysis of erythrocytes from livestock, whereby a residue containing erythrocyte membranes is obtained;

(2) washing the residue containing erythrocyte membranes with dichloromethane to remove cholesterol;

(3) extracting sphingomyelin from the erythrocyte membranes in the washed residue; and (4) subjecting the obtained sphingomyelin to enzymolysis with sphingomyelinase produced by *Bacillus cereus* to obtain N-lignoceroylsphingosine.

2. The process according to claim 1, wherein the sphingomyelinase is provided by using a bacteria culture of *Bacillus cereus* which is placed in contact with the sphingomyelin.

3. The process according to claim 1, wherein the sphingomyelin is extracted from a bacteria culture of *Bacillus cereus*.

4. The process according to claim 1, wherein step (4) is repeated at least one time.

* * * * *